United States Patent
Ida et al.

(10) Patent No.: US 9,913,622 B2
(45) Date of Patent: Mar. 13, 2018

(54) X-RAY CT APPARATUS AND IMAGE PROCESSING DEVICE

(71) Applicant: Toshiba Medical Systems Corporation, Otawara-shi (JP)

(72) Inventors: Takashi Ida, Kawasaki (JP); Toshiyuki Ono, Kawasaki (JP); Shuhei Nitta, Ota (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 141 days.

(21) Appl. No.: 15/045,968

(22) Filed: Feb. 17, 2016

(65) Prior Publication Data

US 2016/0242720 A1     Aug. 25, 2016

(30) Foreign Application Priority Data

Feb. 23, 2015  (JP) ................................ 2015-033362
Dec. 25, 2015  (JP) ................................ 2015-255000

(51) Int. Cl.
*A61B 6/03*  (2006.01)
*A61B 6/00*  (2006.01)
*G06T 11/00*  (2006.01)

(52) U.S. Cl.
CPC ............ *A61B 6/5205* (2013.01); *A61B 6/032* (2013.01); *A61B 6/405* (2013.01); *A61B 6/4241* (2013.01); *A61B 6/482* (2013.01); *G06T 11/003* (2013.01)

(58) Field of Classification Search
CPC ..... A61B 5/7278; A61B 6/032; A61B 6/4241; A61B 6/482; A61B 6/5205; A61B 6/5211; A61B 6/5217; G01T 1/36; G06T 11/003; G06T 2211/408
See application file for complete search history.

(56) References Cited

U.S. PATENT DOCUMENTS

| | | | |
|---|---|---|---|
| 8,160,206 B2 | 4/2012 | Wu et al. | ..................... 378/98.9 |
| 8,260,023 B2 | 9/2012 | Thomsen et al. | ............. 382/131 |
| 2013/0287260 A1 | 10/2013 | Taguchi et al. | ........ G06T 11/003 |
| 2014/0321603 A1* | 10/2014 | Taguchi et al. | ........ A61B 6/482 378/5 |

(Continued)

FOREIGN PATENT DOCUMENTS

| JP | 2010-125332 A | 6/2010 |
|---|---|---|
| JP | 2011-139899 A | 7/2011 |

(Continued)

*Primary Examiner* — Andrew W Johns
(74) *Attorney, Agent, or Firm* — Oblon, McClelland, Maier & Neustadt, L.L.P.

(57) ABSTRACT

According to an embodiment, an X-ray computed tomography (CT) apparatus includes processing circuitry. The processing circuitry is configured to acquire projection data that is based on a spectrum representing an amount of X-rays with respect to energy of a radiation having passed through a subject; select a plurality of materials; generate, from the projection data, first density images for each of the selected materials; generate a monochromatic image of specific energy from the first density images; reconstruct the projection data corresponding to the specific energy to generate a reconstructed image; compare the monochromatic image and the reconstructed image; and provide a notification indicating a result of the comparison.

18 Claims, 10 Drawing Sheets

(56) References Cited

U.S. PATENT DOCUMENTS

2015/0272527 A1\* 10/2015 Narayanan et al. ... A61B 6/482
                                                      382/131

FOREIGN PATENT DOCUMENTS

| JP | 2011-139899 A5 | 7/2011 |
| JP | 2011-172803 A  | 9/2011 |
| JP | 2013-81765 A   | 5/2013 |
| JP | 2013-81765 A5  | 5/2013 |
| JP | 2015-198833 A  | 11/2015 |

\* cited by examiner

MATERIAL SPECIFICATION PRIORITY TABLE ~2000

| PRIORITY | NAME OF MATERIAL |
|---|---|
| 1 | WATER |
| 2 | IODINE |
| 3 | CALCIUM |
| 4 | FAT |
| ⋮ | ⋮ |

… (1)

X-RAY CT APPARATUS AND IMAGE PROCESSING DEVICE

CROSS-REFERENCE TO RELATED APPLICATIONS

This application is based upon and claims the benefit of priority from Japanese Patent Application No. 2015-033362, filed Feb. 23, 2015; and Japanese Patent Application No. 2015-255000, filed Dec. 25, 2015, the entire contents of which are incorporated herein by reference.

FIELD

Embodiments described herein relate generally to an X-ray CT device and an image processing device.

BACKGROUND

In recent years, silicon-based photomultipliers have been actively developed, and radiation detection devices such as an X-ray computed tomography (CT) apparatus including a photomultiplier have been also developed. In the X-ray CT device, X-rays that have penetrated through a subject are detected, and a sectional image (reconstructed image) of the subject using a CT value corresponding to an X-ray attenuation factor as a pixel value is reconstructed. Specifically, the X-ray attenuation factor at the time when the X-rays pass through a material (subject) varies depending on the type of the material such as a bone or water, so that an internal structure of the subject is visualized by reconstructing the attenuation factor with the cross section of the subject based on projection data obtained by a detector for detecting intensity of the X-rays passing through the subject while rotating around the subject.

In recent years, to grasp the inside of the subject in more detail, X-ray CT devices that calculate density of each material from the projection data have been in practical use. To calculate such density, known is a method of obtaining density images of two materials by projecting images twice by switching a tube voltage of an X-ray tube in two different ways, using a dual energy CT device because the attenuation factor varies depending on the energy and the density of the material even with the same material. The X-rays include photons having various pieces of energy, and energy distribution varies as the tube voltage varies. In the above method, the density images of the two materials are obtained through the following two routes.
(1) Projection data of two types of tube voltages→attenuation factor images of two types of tube voltages→density images of two materials
(2) Projection data of two types of tube voltages→X-ray transmission lengths of two types of materials→density images of two materials An image (reconstructed image) having, as a pixel value, a linear attenuation coefficient that is an attenuation factor per unit length of the X-ray or a CT value that is a relative value of the linear attenuation coefficient of air, water, and the like is referred to as an attenuation factor image, and an image having the density of the material as a pixel value is referred to as a density image. The linear attenuation coefficient is uniquely determined based on the type and the density of the material, and the energy of the photons, and the attenuation factor image assuming specific energy can be synthesized from the obtained density of the two types of materials. The attenuation factor image is referred to as a monochromatic image. Contrast of the material of interest can be improved by adjusting the energy for synthesizing the monochromatic image.

DETAILED DESCRIPTION

Figure 1:
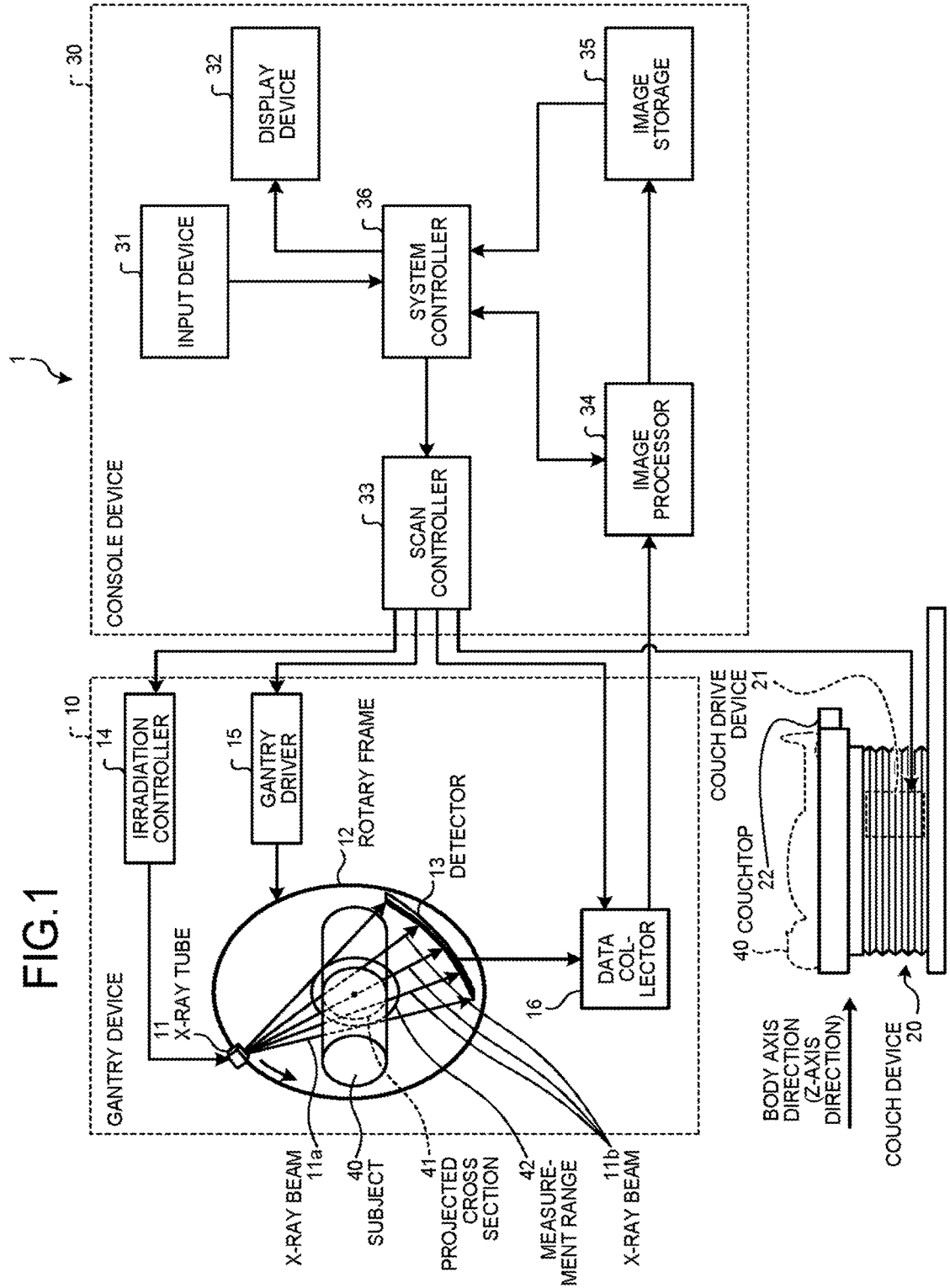
FIG. 1 is an entire configuration diagram of an X-ray inspecting device according to a first embodiment.

According to an embodiment, an X-ray CT device includes an acquirer, a first generator, an X-ray computed tomography (CT) apparatus includes processing circuitry. The processing circuitry is configured to acquire projection data that is based on a spectrum representing an amount of X-rays with respect to energy of a radiation having passed through a subject; select a plurality of materials; generate, from the projection data, first density images for each of the selected materials; generate a monochromatic image of specific energy from the first density images; reconstruct the projection data corresponding to the specific energy to generate a reconstructed image; compare the monochromatic image and the reconstructed image; and provide a notification indicating a result of the comparison.

The following describes an X-ray CT device and an image processing device according to preferred embodiments in detail with reference to the accompanying drawings. In the drawings referred to hereinafter, the same components are denoted by the same reference numerals. However, the drawings are schematic, and a specific configuration needs to be determined in consideration of the following description.

First Embodiment

FIG. 1 is an entire configuration diagram of an X-ray inspecting device according to a first embodiment. With reference to FIG. 1, the following schematically describes the entire configuration of this X-ray inspecting device 1.

As illustrated in FIG. 1, the X-ray inspecting device 1 as an example of the X-ray CT device is a spectral CT device, a photon counting CT device, or the like that causes X-rays as an example of radiations to penetrate through a subject 40 to be detected as a spectrum represented by the number of photons per energy, and obtains a sectional image of a projected cross section 41 of the subject 40 in a measurement range 42. The X-ray inspecting device 1 includes, as illustrated in FIG. 1, a gantry device 10, a couch device 20, and a console device 30 (image processing device).

The gantry device 10 is a device that irradiates the subject 40 with the X-rays to penetrate therethrough, and can detect the spectrum described above. The gantry device 10 includes an X-ray tube 11, a rotary frame 12, a detector 13, an irradiation controller 14, a gantry driver 15, and a data collector 16.

The X-ray tube 11 is a vacuum tube that generates X-rays with a high voltage supplied from the irradiation controller 14, and irradiates the subject 40 with X-ray beams 11a. The spectrum represented by the number of photons per energy of the X-rays emitted from the X-ray tube 11 is determined depending on the tube voltage and the tube current of the X-ray tube 11 and the type of a target used as a radiation source (for example, tungsten). The energy of the X-rays emitted from the X-ray tube 11 is attenuated (the number of photons for each piece of energy of the X-rays is reduced) corresponding to a state of a material constituting the subject 40 when the X-rays are penetrating through the subject 40, the number of photons for each piece of energy is reduced, and the spectrum is changed.

The rotary frame 12 is a ring-shaped support member that supports the X-ray tube 11 and the detector 13 to be opposed to each other across the subject 40.

Figure 3:
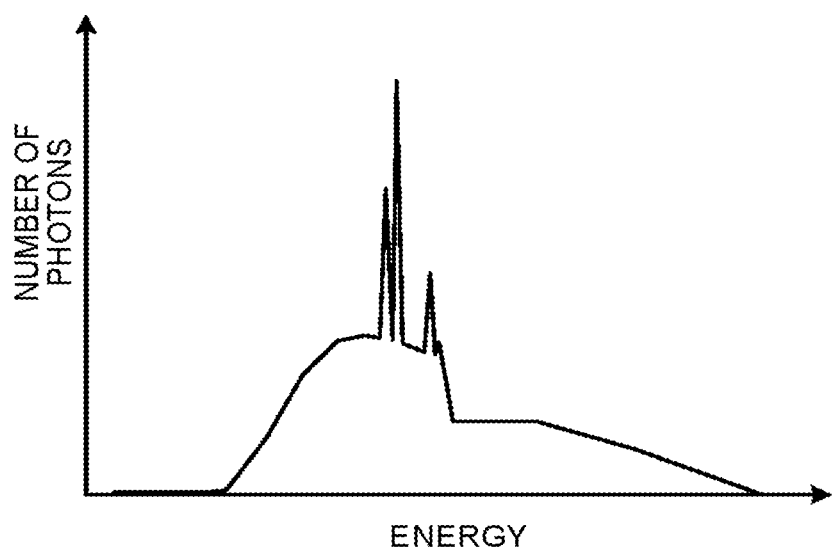
FIG. 3 is a diagram illustrating an example of a spectrum of energy detected in a specific channel.

The detector 13 is a detector for detecting, for each channel, the number of photons per energy of X-ray beams 11b as the X-rays that are emitted from the X-ray tube 11 and have penetrated through the subject 40. In other words, the detector 13 can detect the spectrum represented by the number of photons per energy of the X-rays as illustrated in FIG. 3 described later for each channel. Hereinafter, the spectrum detected by the detector 13 may be referred to as a "detected spectrum" in some cases. As illustrated in FIG. 1, the detector 13 can detect the spectrum for each view while rotating in the circumferential direction of the rotary frame 12. In this case, the view means an angle in a case in which the spectrum is detected by the detector 13 for each predetermined angle in a circuit of 360° in the circumferential direction of the rotary frame 12. In other words, when the detector 13 detects the spectrum for every 0.5°, 1 view=0.5° is assumed. The detector 13 is a two-dimensional array type detector in which a plurality of detection element arrays including a plurality of detection elements arranged in a channel direction (the circumferential direction of the rotary frame 12) are arranged along a body axis direction (slice direction) (Z-axis direction illustrated in FIG. 1) of the subject 40. The detection element array of the detector 13 may include a combination of a photo-counting-type detection element and an integration-type detection element. Alternatively, a plurality of sets of the X-ray tube 11 and the detector 13 may be arranged.

The irradiation controller 14 is a device that generates a high voltage, and supplies the generated high voltage to the X-ray tube 11.

The gantry driver 15 rotationally drives the rotary frame 12 to rotationally drive the X-ray tube 11 and the detector 13 on a circular orbit centering on the subject 40. The configuration of the gantry driver 15 is not limited to a configuration of rotationally driving both of the X-ray tube 11 and the detector 13. For example, the detector 13 may be configured such that detection elements are arranged in the circumferential direction of the rotary frame 12 over one circuit, and the gantry driver 15 may rotationally drive only the X-ray tube 11.

The data collector 16 is a device that collects pieces of data of the spectrum represented by the number of photons per energy detected by the detector 13 for each channel. The data collector 16 performs amplification processing, A/D conversion processing, or the like on each piece of the collected data of the spectrum, and outputs the data to the console device 30. For example, the data collector 16 outputs the data, which is obtained by performing amplification processing, A/D conversion processing, or the like on the collected pieces of data of the spectrum, to the console device 30 as a sinogram (subject sinogram) for each energy band (energy bin) (hereinafter, simply referred to as "for each energy" in some cases) having a predetermined width.

The couch device 20 is a device on which the subject 40 can be placed, and includes a couch drive device 21 and a couchtop 22 as illustrated in FIG. 1.

The couchtop 22 is a couch such as a bed on which the subject 40 is placed. The couch drive device 21 is a device moved in the body axis direction (Z-axis direction) of the subject 40 placed on the couchtop 22 to move the subject 40 into the rotary frame 12.

The console device 30 is a device that receives an operation on the X-ray inspecting device 1 by an operator and reconstructs a sectional image (restored image) from the pieces of data collected by the gantry device 10. As illustrated in FIG. 1, the console device 30 includes an input device 31, a display device 32, a scan controller 33, an image processor 34, an image storage 35, and a system controller 36.

The input device 31 is a device by which an operator who is operating the X-ray inspecting device 1 can input various instructions by operation. The input device 31 transmits various commands input by operation to the system controller 36. Examples of the input device 31 include a mouse, a keyboard, a button, a trackball, and a joystick.

The display device 32 is a device that displays a graphical user interface (GUI) for receiving an operation instruction from the operator via the input device 31, and displays a restored image (sectional image) stored in the image storage 35 described later. Examples of the display device 32 include a cathode ray tube (CRT) display, a liquid crystal display (LCD), and an organic electro-luminescence (EL) display.

The scan controller 33 is a processing unit that controls operations of the irradiation controller 14, the gantry driver 15, the data collector 16, and the couch drive device 21. Specifically, the scan controller 33 causes the X-rays to be continuously or intermittently emitted from the X-ray tube 11 while causing the rotary frame 12 to be rotated to perform X-ray scanning. For example, the scan controller 33 causes helical scanning or non-helical scanning to be performed. The helical scanning is performed for imaging by continuously rotating the rotary frame 12 while moving the couchtop 22. The non-helical scanning is performed such that the rotary frame 12 rotates around the subject 40 once to perform imaging, and subsequently the rotary frame 12 rotates around it once more to perform imaging while shifting the couchtop 22 on which the subject 40 is placed by a predetermined amount.

The image processor 34 is a processing unit that reconstructs a sectional image of the subject from the sinogram received from the data collector 16. Details about an operation and a block configuration of the image processor 34 will be described later.

The image storage 35 is a functional unit that stores therein sectional images (restored images) generated through reconstruction processing performed by the image processor 34. Examples of the image storage 35 include a hard disk drive (HDD), a solid state drive (SSD), and an optical disc.

The system controller 36 controls operations of the gantry device 10, the couch device 20, and the console device 30 to control the entire X-ray inspecting device 1. Specifically, the system controller 36 controls the scan controller 33 to control an operation of collecting the data of the spectrum of the subject 40 performed by the gantry device 10 and the couch device 20. The system controller 36 controls the image processor 34 to control the reconstruction processing on sectional images. The system controller 36 reads out the sectional images from the image storage 35, and causes the display device 32 to display the sectional images.

The sinogram for each predetermined energy band is assumed to be generated from the collected data of the spectrum by the data collector 16. However, embodiments are not limited to this. In other words, the data collector 16 may transmit the collected data of the spectrum to the image processor 34, and the image processor 34 may generate a sinogram for each energy band having a predetermined width from the data of the spectrum.

Figure 2:
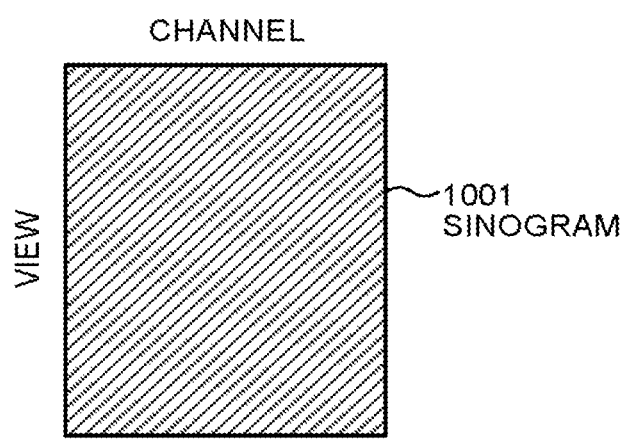
FIG. 2 is a diagram for explaining a sinogram.
Figure 4:
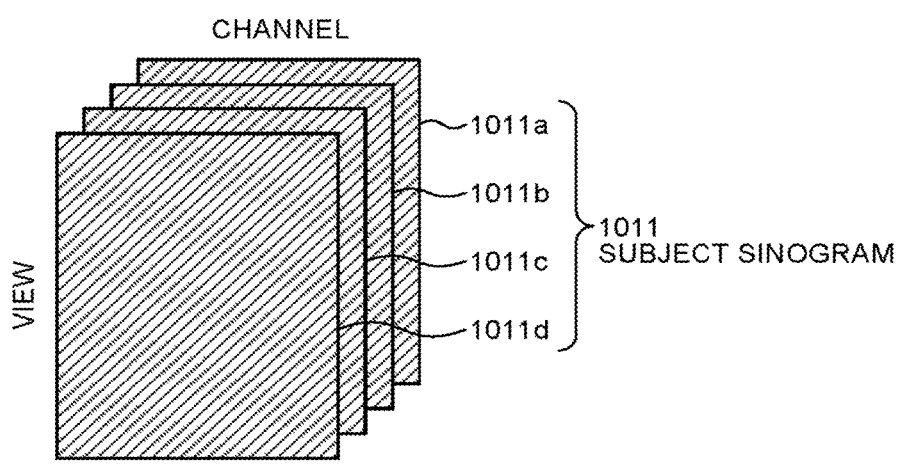
FIG. 4 is a diagram illustrating an example of a subject sinogram.

FIG. 2 is a diagram for explaining the sinogram. FIG. 3 is a diagram illustrating an example of the spectrum of the energy detected in a specific channel. FIG. 4 is a diagram illustrating an example of the subject sinogram. With reference to FIGS. 2 to 4, the following describes the sinogram and the spectrum detected by the detector 13.

The data collector 16 of the gantry device 10 generates a sinogram from the spectrum that is detected by the detector 13 and represented by the number of photons for each energy as illustrated in FIG. 3. The sinogram is data in which a measurement value for each view of the X-ray tube 11 and for each channel of the detector 13 is arranged as a pixel value as illustrated in FIG. 2 as a sinogram 1001. In the following description, the measurement value for each view and for each channel is assumed to be a pixel value, and the sinogram is assumed to be an image. In this case, a sinogram generated from the spectrum (refer to FIG. 3) obtained when the X-ray is emitted from the X-ray tube 11 and penetrates through the subject 40 to be detected by the detector 13 is referred to as a subject sinogram. A sinogram generated from the spectrum obtained when the X-ray passes through only the air and is detected by the detector 13 without placing the subject 40 is referred to as an air sinogram. Each of the pixel values of the subject sinogram and the air sinogram is, for example, the number of photons detected by the detector 13 as a measurement value.

The detector 13 can detect the spectrum represented by the number of photons for each energy for each view and each channel, so that the data collector 16 can obtain a subject sinogram 1011 for each energy as illustrated in FIG. 4 through X-ray scanning for one circuit of the X-ray tube 11. An example illustrated in FIG. 4 illustrates a case in which the spectrum is divided into four energy bands and four subject sinograms 1011a to 1011d are obtained for each energy band. While FIG. 4 illustrates the example in which the spectrum is divided into four energy bands, the number of divisions is not limited to four. In view of improvement in the S/N ratio of a restored image (attenuation factor image) and a density image described later, the number of photons in the energy band used in reconstruction and estimation of material density may be preferably uniform in some cases. To achieve this, the following two methods can be used, for example.

First method: In generating a sinogram, the spectrum is divided into energy bands in which the number of photons is uniform.

Second method: The spectrum is finely divided first (for example, divided per 1 [keV]), and the numbers of photons are totaled when reconstruction or estimation of the density of the material is performed.

Figure 5:
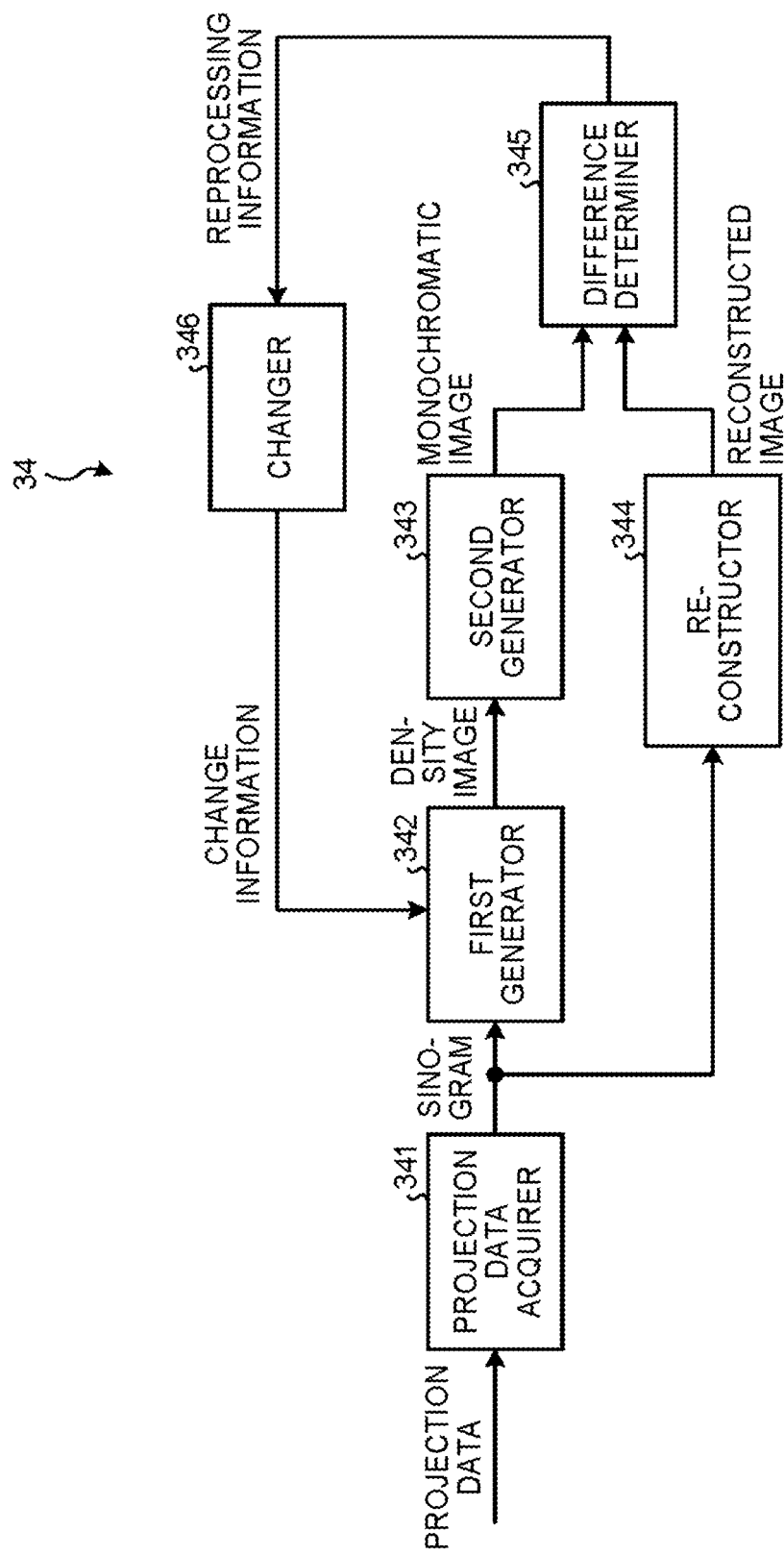
FIG. 5 is a diagram illustrating an example of a block configuration of an image processor according to the first embodiment.
Figures 6, 7:
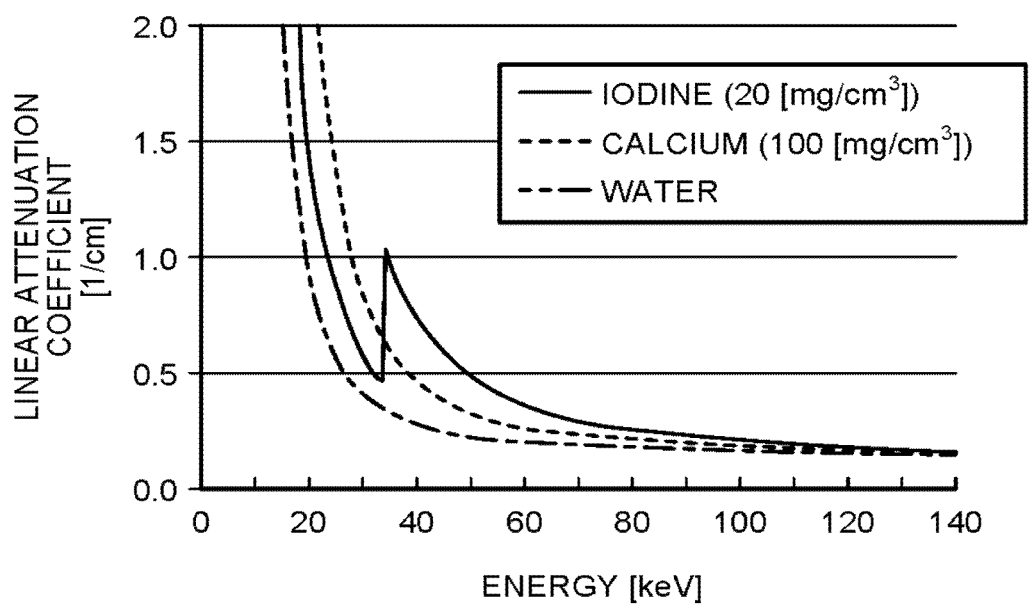
FIG. 6 is a diagram illustrating an example of characteristics of a linear attenuation coefficient with respect to energy of X-rays.
FIG. 7 is a diagram illustrating a configuration example of a material specification priority table.

FIG. 5 is a diagram illustrating an example of a block configuration of the image processor according to the first embodiment. FIG. 6 is a diagram illustrating an example of characteristics of a linear attenuation coefficient with respect to the energy of the X-rays. FIG. 7 is a diagram illustrating a configuration example of a material specification priority table. With reference to FIGS. 5 to 7, the following describes the block configuration of the image processor 34 according to the embodiment and an operation of each block.

As illustrated in FIG. 5, the image processor 34 includes a projection data acquirer 341, a first generator 342, a second generator 343, a reconstructor 344, a difference determiner 345 (first comparator, first determiner), and a changer 346.

The projection data acquirer 341 is a functional unit that receives and acquires a subject sinogram that is a sinogram of the subject 40 as projection data from the data collector 16. The subject sinogram acquired by the projection data acquirer 341 is a sinogram generated by the data collector 16 as described above for each energy (a sinogram per energy).

The first generator 342 is a functional unit that sets materials that are possibly present in the subject 40, and generates a density image for each of the set materials using the subject sinogram received from the projection data acquirer 341. In the following description, the density of the density image is assumed to represent a mass (for example, [mg/cm$^3$] is used as a unit) of a specific material included per unit volume. In a case in which the subject 40 is a human body or an animal, the material to be set is assumed to be water, bones, or fat; a contrast medium when the contrast medium is injected into the subject 40; calcium, a thrombus, and fibers of a blood vessel wall in a plaque of a blood vessel; and metals disposed in the interior of the body such as a stent.

First, with reference to FIG. 6, the following describes the characteristics of the linear attenuation coefficient of the material with respect to the energy of X-rays. FIG. 6 illustrates the characteristics of iodine as a kind of the contrast medium, calcium, and water as examples of the characteristics of the linear attenuation coefficient with respect to the energy of X-rays. Specifically, FIG. 6 illustrates the characteristics for iodine the density of which is 20 [mg/cm$^3$], for calcium the density of which is 100 [mg/cm$^3$], and for water the concentration of which is 100 [%]. As illustrated in FIG. 6, the linear attenuation coefficient is continuously reduced as the energy increases for any material in principle. However, as illustrated in FIG. 6 as the characteristic of iodine, the linear attenuation coefficient discontinuously increases when the energy exceeds a level at which the photoelectric effect occurs such as a K-absorption edge. The energy at the K-absorption edge differs for each element, and is about 33 [keV] for iodine as illustrated in FIG. 6. In this way, the characteristics of the linear attenuation coefficient with respect to the energy differ for each material.

As described below, the first generator 342 calculates the density for each of the set materials utilizing the characteristics of the linear attenuation coefficients of the materials with respect to the energy of X-rays, and generates a density image. Assuming that the linear attenuation coefficient of energy E of X-rays at coordinates (x, y) of an attenuation factor image (restored image, reconstructed image) is μ(x, y, E), the density of the density image of a material M at the coordinates (x, y) is ρ(x, y, M), the linear attenuation coefficient of the energy E when the concentration of the material M is 100 [%] is $(\mu)_M(E)$, and the density when the concentration of the material M is 100 [%] $(\rho)_M$, the linear attenuation coefficient μ(x, y, E) is represented by the following Equation (1).

$$\mu(x, y, E) = \sum_M \rho(x, y, M) \cdot \frac{(\mu)_M(E)}{(\rho)_M} \quad (1)$$

The values of the linear attenuation coefficient $(\mu)_M(E)$ and the density $(\rho)_M$ in Equation (1) are known as theoretical values of the material M. In Equation (1), $(\mu)_M(E)/(\mu)_M$ corresponds to what is called a mass attenuation coefficient. Specifically, the first generator 342 first sets a specific energy band, receives a subject sinogram of the set energy band from the projection data acquirer 341, and generates an attenuation factor sinogram from the received subject sinogram. Specifically, the first generator 342 calculates an attenuation factor for each view and each channel of the subject sinogram of the set energy band, and generates an attenuation factor sinogram using the attenuation factor as the pixel value. The energy band to be set is, for example, 30 to 32 [keV], 34 to 36 [keV], and 60 to 62 [keV]. The energy band to be set may be a certain piece of energy. However, if an energy band combining a plurality of continuous pieces of energy is used, accuracy in reconstruction can be improved because the number of photons is increased. When the number of photons of the X-rays emitted from the X-ray tube 11 is already known, the attenuation factor is calculated for each view and each channel as follows: the attenuation factor=(the number of photons emitted from the X-ray tube 11 in the channel and the view)/(the number of photons penetrating through the subject 40 and detected by the detector 13 in the channel and the view). On the other hand, when the number of photons of the X-rays emitted from the X-ray tube 11 is unknown, the first generator 342 inputs in advance the spectrum detected by the detector 13 without placing the subject 40, and generates an air sinogram from the spectrum. The attenuation factor is then calculated for each view and each channel as follows: the attenuation factor=(the number of photons (pixel value) of the air sinogram)/(the number of photons (pixel value) of the subject sinogram). When the number of photons in a case in which the subject 40 is placed is assumed to be A and the number of photons in a case in which the subject 40 is not placed is assumed to be B, for example, log(B/A) can be calculated to be the pixel value (attenuation factor) of the attenuation factor sinogram.

Next, the first generator 342 reconstructs the generated attenuation factor sinogram using back projection or successive approximation, which are known techniques, and obtains the linear attenuation coefficient μ(x, y, E). The linear attenuation coefficient varies depending on the type and the density of the material through which the X-rays penetrate, so that the internal structure of the subject 40 can be recognized by visualizing the distribution of the linear attenuation coefficient in a reconstructed image.

When back projection is employed as a reconstruction method as described above, first, a measurement value detected by the detector 13 in a certain view is written to the entire image to be reconstructed. This process is performed for all views. In this case, values remain at places where the subject 40 is not present, whereby a blurred image is obtained. However, a clear reconstructed image is obtained by performing filter processing with a filter that emphasizes edges and reduces artifacts to emphasize the edges and cancel blurring. A method of filter processing may be any of a method in which the processing is performed in a frequency region after Fourier transformation, or a method in which the processing is performed through a convolution in a real space. Such a method of correcting the reconstructed image using the filter is specifically referred to as a filtered back projection (FBP) method.

When successive approximation is employed as the reconstruction method, first, a temporary image is prepared in advance, and the X-rays are emitted in each view. If the pixel value of the temporary image is smaller than a measurement value actually detected by the detector 13, the pixel value of the temporary image is increased. In contrast, if the pixel value of the temporary image is larger than the measurement value actually detected by the detector 13, the pixel value of the temporary image is reduced. By repeating these processes, the pixel value of the temporary image is changed to be equal to the pixel value of a true sectional image, whereby a reconstructed image is obtained. Examples of successive approximation include various methods such as an ordered subset expectation maximization (OS-EM) method and a maximum likelihood expectation maximization (ML-EM) method.

Next, the first generator 342 establishes simultaneous equations in which only the density ρ(x, y, M) is unknown through Equation (1) using the obtained linear attenuation coefficient μ(x, y, E), and causes the number of the set energy bands to be equal to the number of the set materials to calculate the density ρ(x, y, M) as a solution for each set of coordinates (x, y). The first generator 342 then generates a density image in which the calculated density ρ(x, y, M) is arranged as the pixel value for each set of coordinates (x, y). The first generator 342 transmits the generated density image to the second generator 343.

Typically, the obtained linear attenuation coefficient μ(x, y, E) includes an error, so that the error in the density ρ(x, y, M) can be reduced by causing the number of the set energy bands to be larger than the number of the set materials to increase the number of equations, and using a method of least squares and the like. The linear attenuation coefficient μ(x, y, E) is an average value in the set energy band, so that the linear attenuation coefficient $(\mu)_M(E)$ is also caused to be an average value in the energy band.

Assuming that the material set by the first generator 342 is a material that is not actually present in the subject 40, it is ideal that the density of the material that is not present be 0, and the density of the material that is present be correctly calculated. However, the calculated density may actually include an error due to a measurement error, a calculation error, and the like. The error in the density increases as the number of unknown materials increases. Thus, by excluding the material that is unlikely to be present or is present in a trace amount from a target to be set to minimize the number of the materials, the density of a main material can be obtained with high accuracy.

The second generator 343 is a functional unit that substitutes the density ρ of the density image received from the first generator 342 in the right side of Equation (1) described above, sets specific energy (hereinafter, also referred to as "difference comparison energy" in some cases), and calculates the linear attenuation coefficient μ(x, y, E) of the difference comparison energy using $(\mu)_M(E)/(\rho)_M$ of the set difference comparison energy. The second generator 343 then generates a monochromatic image in which the calculated linear attenuation coefficient μ(x, y, E) is arranged as the pixel value for each set of coordinates (x, y). The second generator 343 transmits the generated monochromatic image to the difference determiner 345.

The difference comparison energy set by the second generator 343 may be identical to the energy set by the first generator 342.

The reconstructor 344 is a functional unit that reconstructs a subject sinogram received from the projection data acquirer 341 to generate a reconstructed image. Specifically, the reconstructor 344 first receives a subject sinogram of the difference comparison energy set by the second generator 343 from the projection data acquirer 341, and generates an attenuation factor sinogram from the received subject sinogram. The method of generating an attenuation factor sinogram by the reconstructor 344 is the same as the method of generating an attenuation factor sinogram by the first generator 342 described above.

The reconstructor 344 reconstructs the generated attenuation factor sinogram using back projection, successive approximation, or the like, which are known techniques, to generate a reconstructed image. The reconstructor 344 transmits the generated reconstructed image to the difference determiner 345. The reconstructed image generated by the reconstructor 344 may include noise because the reconstructed image is generated based on the subject sinogram of the difference comparison energy as specific energy, that is, the subject sinogram based on the energy in which the number of photons is small. However, the linear attenuation coefficient as the pixel value thereof can be assumed to be a correct value.

The difference determiner 345 is a functional unit that obtains a difference (first difference) that is a result of comparison between the monochromatic image generated by the second generator 343 and the reconstructed image generated by the reconstructor 344, and makes a determination on the difference.

When the density is correctly calculated by the first generator 342, the difference between the pixel values of the monochromatic image of the difference comparison energy generated by the second generator 343 using the density and the reconstructed image of the difference comparison energy generated by the reconstructor 344 is substantially 0. On the other hand, when the density calculated by the first generator 342 is incorrect, the monochromatic image is different from the reconstructed image, so that a difference is caused.

Accordingly, if the sum total of absolute values of differences among the pixel values of the entire monochromatic image and reconstructed image is equal to or smaller than a predetermined value (first predetermined value), the difference determiner 345 determines that the density of the density image generated by the first generator 342 has sufficiently high accuracy. On the other hand, if the sum total of the absolute values of the differences is larger than the predetermined value, the difference determiner 345 determines that the accuracy in the density of the density image is insufficient, generates reprocessing information including information indicating that the density needs to be obtained again (hereinafter, also referred to as "reprocessed") by the first generator 342, and transmits the reprocessing information to the changer 346.

In the above description, the difference determiner 345 is used to obtain the sum total of the absolute values of the differences among the pixel values. However, embodiments are not limited to this. For example, another error scale may be used such as the sum of squares of the differences among the pixel values.

In the above description, the difference determiner 345 obtains the differences among the pixel values of the entire monochromatic image and reconstructed image. However, embodiments are not limited to this. When there is a region of interest such as a blood vessel in the image, the differences among the pixel values in the region of interest may be obtained.

The difference determiner 345 may obtain the differences for each region or each pixel in the monochromatic image and the reconstructed image, and cause the reprocessing information to include necessity for reprocessing for each region or each pixel.

The result of comparison (for example, information on the difference) between the monochromatic image and the reconstructed image obtained by the difference determiner 345 may be displayed, for example, on the display device 32 (an example of a first notifier). In this case, a method for sending a notification indicating the result of comparison is not limited to the display on the display device 32. For example, the result of comparison may be provided with audio output by an audio output device (an example of the first notifier) not illustrated, or provided with lighting or flashing of a lamp by a lamp display device (an example of the first notifier).

The changer 346 is a functional unit that changes a setting of the material the density of which is calculated or the energy band in which the linear attenuation coefficient μ is obtained according to the reprocessing information received from the difference determiner 345. Specifically, the changer 346 generates change information for changing the setting of the material the density of which is calculated or the energy band in which the linear attenuation coefficient μ is obtained, and transmits the change information to the first generator 342. The first generator 342 changes the setting of the material or the setting of the energy band in which the linear attenuation coefficient μ is obtained according to the change information received from the changer 346, and calculates again the density of each material after the setting is changed. The second generator 343 generates a monochromatic image again from the density image generated by the first generator 342. The difference determiner 345 obtains the difference between the monochromatic image generated again by the second generator 343 and the reconstructed image generated by the reconstructor 344, and makes a determination on the difference. The series of operations described above is repeated until the accuracy in the density is determined to be sufficiently high or a predetermined number of times is reached while the settings of the material and the energy band are changed by the changer 346.

For example, when a thrombus or fat is assumed not to be present in a plaque and the density is calculated by setting only other materials by the first generator 342 in advance, the changer 346 generates change information for changing the setting to cause the thrombus or the fat to be the material the density of which is calculated. When metal is assumed not to be present in advance, for example, the changer 346 generates change information for changing the setting to cause the metal to be the material the density of which is calculated. To improve accuracy in calculation of the density, for example, the changer 346 generates change information for changing the setting to be the energy band in which a relative relation of magnitude of the linear attenuation coefficients of the materials set by the first generator 342 is different. The energy band of the linear attenuation coefficient μ may be changed by the changer 346 according to a predetermined pattern, for example.

When the changer 346 additionally sets the material the density of which is calculated according to the reprocessing information received from the difference determiner 345, for example, the material may be additionally set according to priority indicated by a material specification priority table 2000 (priority information) in FIG. 7. The material specification priority table 2000 may be, for example, stored in a storage such as the image storage 35 (refer to FIG. 1) in advance. For example, the following describes a case in which the first generator 342 generates a density image assuming and setting the material s assumed to be included in the subject 40 to be water and iodine the priorities of which are 1 and 2, respectively, with reference to the material specification priority table 2000, and the difference determiner 345 determines that the accuracy in the density is insufficient. In this case, the changer 346 assumes that calcium having the next higher priority is included in the subject 40 with reference to the material specification priority table 2000, generates change information to be additionally set, and transmits the change information to the first generator 342. According to the change information, the first generator 342 calculates the density of each material again assuming that the materials included in the subject 40 are water, iodine, and calcium. In the above description, described is the operation of additionally setting the material the density of which is calculated performed by the changer 346. Alternatively, the material having lower priority may be set to be deleted, similarly with reference to the material specification priority table 2000 and the like. As illustrated in FIG. 7, the material specification priority table 2000 is in a table format. Alternatively, the material specification priority table 2000 may be information in any format so long as the information associates materials and priorities.

The setting of the material the density of which is calculated or the energy band in which the linear attenuation coefficient μ is calculated may be changed by the changer 346 according to an operation on the input device 31 by an operator.

When the reprocessing information received from the difference determiner 345 includes the information about necessity for reprocessing for each portion or each pixel of the image, the changer 346 may generate the change information for calculating the density again for each portion or each pixel that needs to be reprocessed using a method similar to the above method.

The difference comparison energy is assumed to be set by the second generator 343. However, the difference comparison energy to be set is not limited to one. In other words, the second generator 343 may set N (N>1) pieces of difference comparison energy, the second generator 343 may generate N monochromatic images, and the reconstructor 344 may generate N reconstructed images. Accordingly, the difference determiner 345 can use the difference of each of N groups of the same difference comparison energy, and check the accuracy in the density in detail for more pieces of energy.

The second generator 343 may generate a monochromatic image while continuously switching magnitude of the difference comparison energy, the reconstructor 344 may generate a reconstructed image while continuously switching the difference energy, and the difference determiner 345 may obtain the difference between the monochromatic image and the reconstructed image for each piece of difference comparison energy that is continuously switched. In this case, when the difference is discontinuously increased at certain energy, an unexpected material having the K-absorption edge at the certain energy is likely to be present, so that the changer 346 may generate the change information for additionally setting the material, and the first generator 342 may additionally set the material to calculate the density again. In this case, the case in which the difference is discontinuously increased at a certain energy may be assumed to be a case in which a change amount of the difference exceeds a predetermined value (second predetermined value), for example. The K-absorption edge is known for each material, so that the material specified when the K-absorption edge is detected is highly likely to be included in the subject 40. Thus, the density of the material is likely to be obtained with high accuracy.

The projection data acquirer 341, the first generator 342, the second generator 343, the reconstructor 344, the difference determiner 345, and the changer 346 illustrated in FIG. 5 are merely conceptual functions, and the configuration is not limited to this. For example, a plurality of functional units illustrated as independent functional units in FIG. 5 may be configured as one functional unit. On the other hand, a function of one functional unit in FIG. 5 may be divided into a plurality of functions to be configured as a plurality of functional units.

Figure 8:
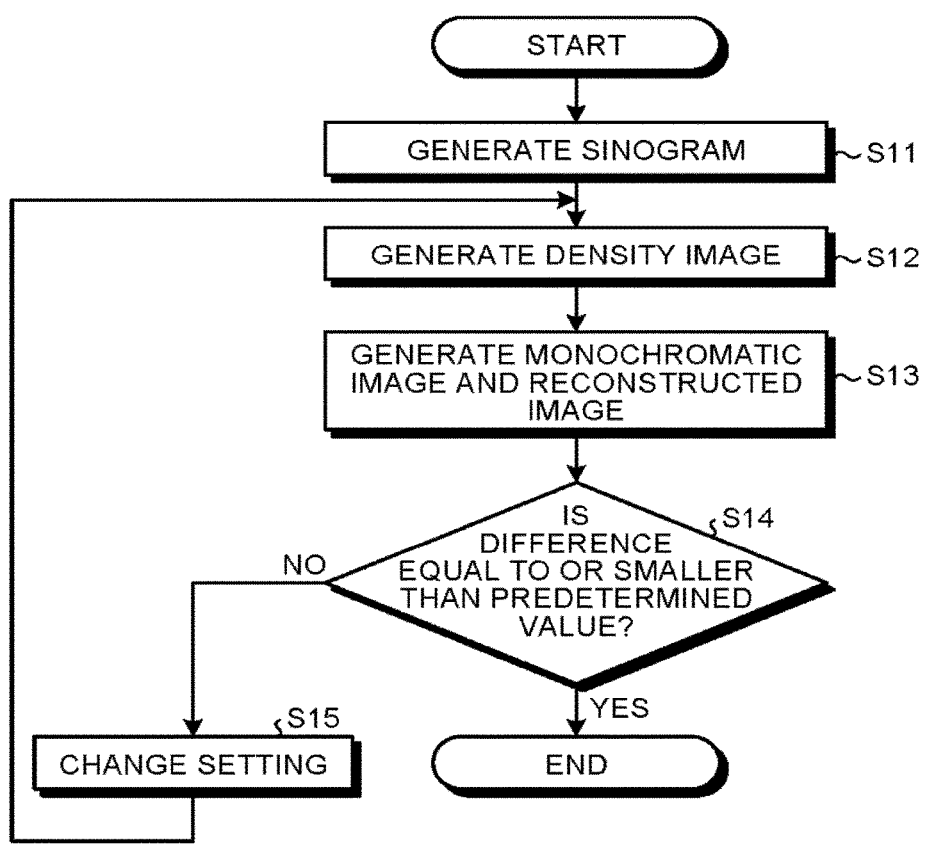
FIG. 8 is a flowchart illustrating an example of an operation of the image processor according to the first embodiment.

FIG. 8 is a flowchart illustrating an example of the operation of the image processor according to the first embodiment. With reference to FIG. 8, the following describes the entire operation of image processing performed by the image processor 34 according to the first embodiment.

Step S11

The projection data acquirer 341 receives and acquires, as the projection data, the subject sinogram as a sinogram of the subject 40 generated by the data collector 16. Then the process proceeds to Step S12.

Step S12

The first generator 342 sets a specific energy band, receives a subject sinogram of the set energy band from the projection data acquirer 341, and generates an attenuation factor sinogram from the received subject sinogram. Next, the first generator 342 reconstructs the generated attenuation factor sinogram using back projection, successive approximation, or the like, which are known techniques, and obtains the linear attenuation coefficient μ(x, y, E). Next, the first generator 342 establishes simultaneous equations in which only the density ρ(x, y, M) is unknown through Equation (1) using the obtained linear attenuation coefficient μ(x, y, E), and causes the number of the set energy bands to be equal to the number of the set materials to calculate the density ρ(x, y, M) as a solution for each set of coordinates (x, y). The first generator 342 then generates a density image in which the calculated density ρ(x, y, M) is arranged as the pixel value for each set of coordinates (x, y). The first generator 342 transmits the generated density image to the second generator 343. Then the process proceeds to Step S13.

Step S13

The second generator 343 substitutes the density ρ of the density image received from the first generator 342 in the right side of Equation (1) described above, sets the difference comparison energy, and calculates the linear attenuation coefficient μ(x, y, E) of the difference comparison energy using $(\mu)_M(E)/(\rho)_M$ of the set difference comparison energy. The second generator 343 then generates a monochromatic image in which the calculated linear attenuation coefficient $\mu(x, y, E)$ is arranged as the pixel value for each set of coordinates (x, y). The second generator 343 transmits the generated monochromatic image to the difference determiner 345.

The reconstructor 344 receives a subject sinogram of the difference comparison energy set by the second generator 343 from the projection data acquirer 341, and generates an attenuation factor sinogram from the received subject sinogram. The reconstructor 344 reconstructs the generated attenuation factor sinogram using back projection, successive approximation, or the like, which are known techniques, to generate a reconstructed image. The reconstructor 344 transmits the generated reconstructed image to the difference determiner 345. Then the process proceeds to Step S14.

Step S14

The difference determiner 345 obtains a difference between the monochromatic image generated by the second generator 343 and the reconstructed image generated by the reconstructor 344, and makes a determination on the difference. For example, if the sum total of the absolute values of the differences among the pixel values of the entire monochromatic image and reconstructed image is equal to or smaller than a predetermined value (Yes at Step S14), the difference determiner 345 determines that the density of the density image generated by the first generator 342 has sufficiently high accuracy, and the image processing is ended. On the other hand, if the sum total of the absolute values of the differences is larger than the predetermined value (No at Step S14), the difference determiner 345 determines that the accuracy in the density of the density image is insufficient, generates reprocessing information including information indicating that reprocessing needs to be performed by the first generator 342, and transmits the reprocessing information to the changer 346. Then the process proceeds to Step S15.

Step S15

The changer 346 changes the setting of the material the density of which is calculated or the energy band in which the linear attenuation coefficient $\mu$ is obtained according to the reprocessing information received from the difference determiner 345. Specifically, the changer 346 generates change information for changing the setting of the material the density of which is calculated or the energy band in which the linear attenuation coefficient $\mu$ is obtained, and transmits the change information to the first generator 342. Then the process proceeds to Step S12.

The series of operations at Steps S12 to S15 are repeated until the accuracy in the density is determined to be sufficiently high while the settings of the material and the energy band are changed by the changer 346 (Step S14). The operations may be repeated until the predetermined number of times is reached as described above.

In this way, the second generator 343 calculates the linear attenuation coefficient $\mu$ of the difference comparison energy as specific energy to generate a monochromatic image, the reconstructor 344 generates, from a subject sinogram of the difference comparison energy, a reconstructed image in which the linear attenuation coefficient as the pixel value is assumed to be correct, and the difference determiner 345 makes a determination on the difference between the monochromatic image and the reconstructed image to determine a matching degree of the monochromatic image and the reconstructed image. In this process, it can be determined that the difference is large and the linear attenuation coefficient as the pixel value of the monochromatic image is not correct, that is, the density of the density image is not accurately calculated, and it can be determined whether a material different from the material that is assumed to be included in the subject 40 is present. If the configuration of the material is determined to be different from that of the material that is assumed to be included in the subject 40, a correct density image can be generated by additionally setting or deleting another material, or changing the setting of the energy band in which the linear attenuation coefficient $\mu$ is obtained.

Modification

Figure 9:
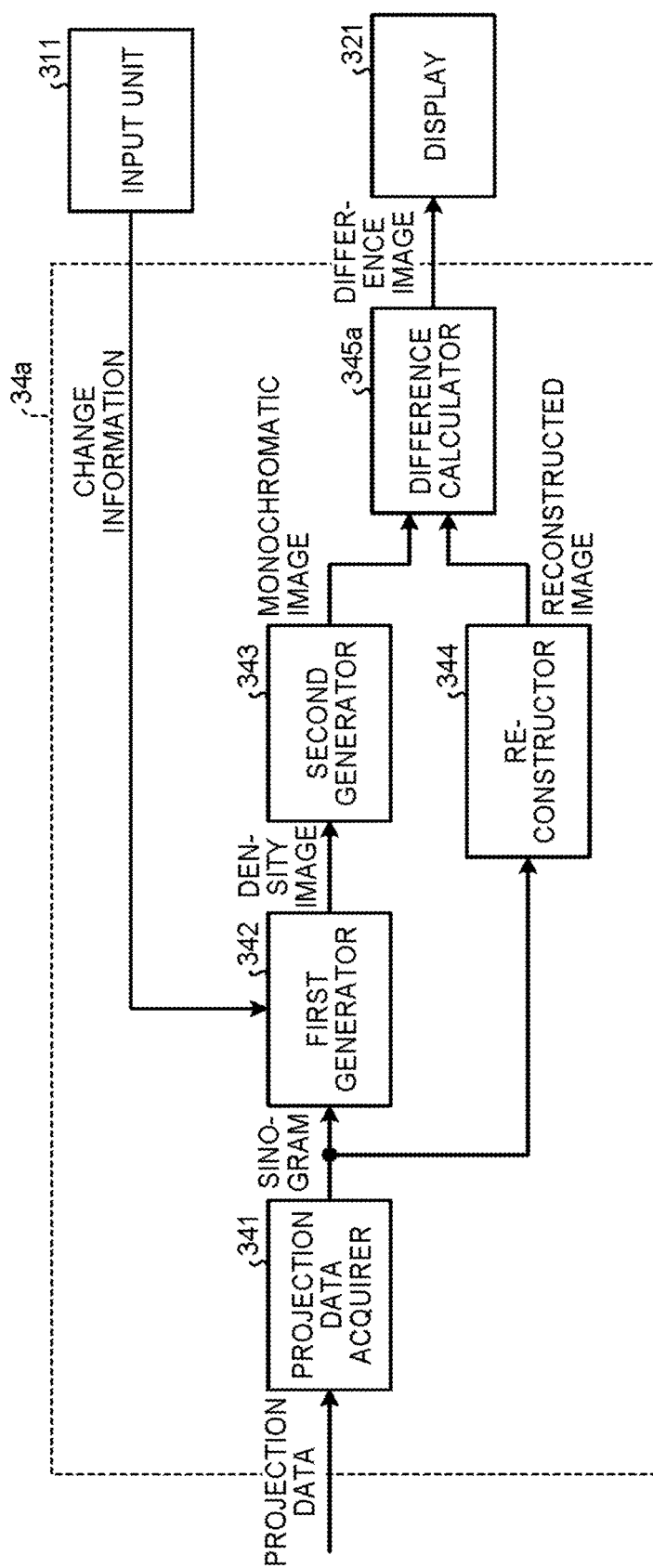
FIG. 9 is a diagram illustrating an example of a block configuration of an image processor according to a modification of the first embodiment.

FIG. 9 is a diagram illustrating an example of a block configuration of the image processor according to a modification of the first embodiment. With reference to FIG. 9, the following describes the block configuration of an image processor 34a according to the modification of the embodiment and the operation of each block, mainly about differences from the image processor 34 according to the first embodiment. The first embodiment describes the operation of automatically generating the change information for changing the setting of the material the density of which is calculated or the energy band in which the linear attenuation coefficient $\mu$ is obtained performed by the changer 346 according to the reprocessing information of the difference determiner 345 if the difference between the monochromatic image and the reconstructed image is larger than the predetermined value. In this modification, described is an operation of manually generating the change information by the operator. In the configuration of the X-ray inspecting device according to the modification, the image processor 34 illustrated in FIG. 1 is replaced with the image processor 34a.

As illustrated in FIG. 9, the image processor 34a includes the projection data acquirer 341, the first generator 342, the second generator 343, the reconstructor 344, and a difference calculator 345a (first calculator). The X-ray inspecting device according to the modification further includes an input unit 311 and a display 321 (an example of the first notifier). The operations of the projection data acquirer 341, the first generator 342, the second generator 343, and the reconstructor 344 of the image processor 34a are the same as the operations of the projection data acquirer 341, the first generator 342, the second generator 343, and the reconstructor 344 of the image processor 34 illustrated in FIG. 5, respectively.

The difference calculator 345a is a functional unit that obtains the difference that is a result of comparison between the monochromatic image generated by the second generator 343 and the reconstructed image generated by the reconstructor 344. For example, the difference calculator 345a obtains the differences among the pixel values of the pixels included in the monochromatic image and the reconstructed image, generates a difference image using each of the differences as the pixel value, and transmits the difference image to the display 321.

The display 321 is a functional unit that displays information on the difference (for example, a difference image) that is a result of comparison between the monochromatic image and the reconstructed image obtained by the difference calculator 345a. The display 321 is implemented with the display device 32 illustrated in FIG. 1.

The input unit 311 is a functional unit through which an operator who has checked the information on the difference between the monochromatic image and the reconstructed image displayed on the display 321 can input the operation of changing the setting of the material the density of which is calculated or the energy band in which the linear attenuation coefficient is obtained. The input unit 311 transmits the change information input by operation to the first generator 342. For example, the operator checks the difference image displayed on the display 321, and manually inputs, via the input unit 311, a portion in which the accuracy in the density should be increased such as a portion of the region of interest in which the difference is large. The input unit 311 transmits the information input by operation to the first generator 342 as the change information. The input unit 311 is implemented with the input device 31 illustrated in FIG. 1.

As described above, the operator checks the information on the difference between the monochromatic image and the reconstructed image on the display 321, and manually inputs the change information by operation via the input unit 311. In this process, an intention of the operator can be reflected in the processing of changing the setting of the material included in the subject 40 and the energy band in which the linear attenuation coefficient is obtained, and the accuracy in the density can be improved along the intention of the operator.

In the above description, the result of comparison (for example, information on the difference) between the monochromatic image and the reconstructed image obtained by the difference calculator 345a is displayed to the operator by the display 321. However, a method for sending a notification indicating the result of comparison is not limited to the display on the display 321. For example, the result of comparison may be provided with audio output by an audio output device (an example of the first notifier) not illustrated, or provided with lighting or flashing of a lamp by a lamp display device (an example of the first notifier).

Second Embodiment

The following describes an image processor according to a second embodiment, mainly about differences from the image processor 34 according to the first embodiment. The first embodiment describes the operation of obtaining the attenuation factor sinogram and the linear attenuation coefficient from the subject sinogram, and generating a density image of the material from the linear attenuation coefficient and the set material. The second embodiment describes an operation of directly generating a density image from the attenuation factor sinogram.

Figure 10:
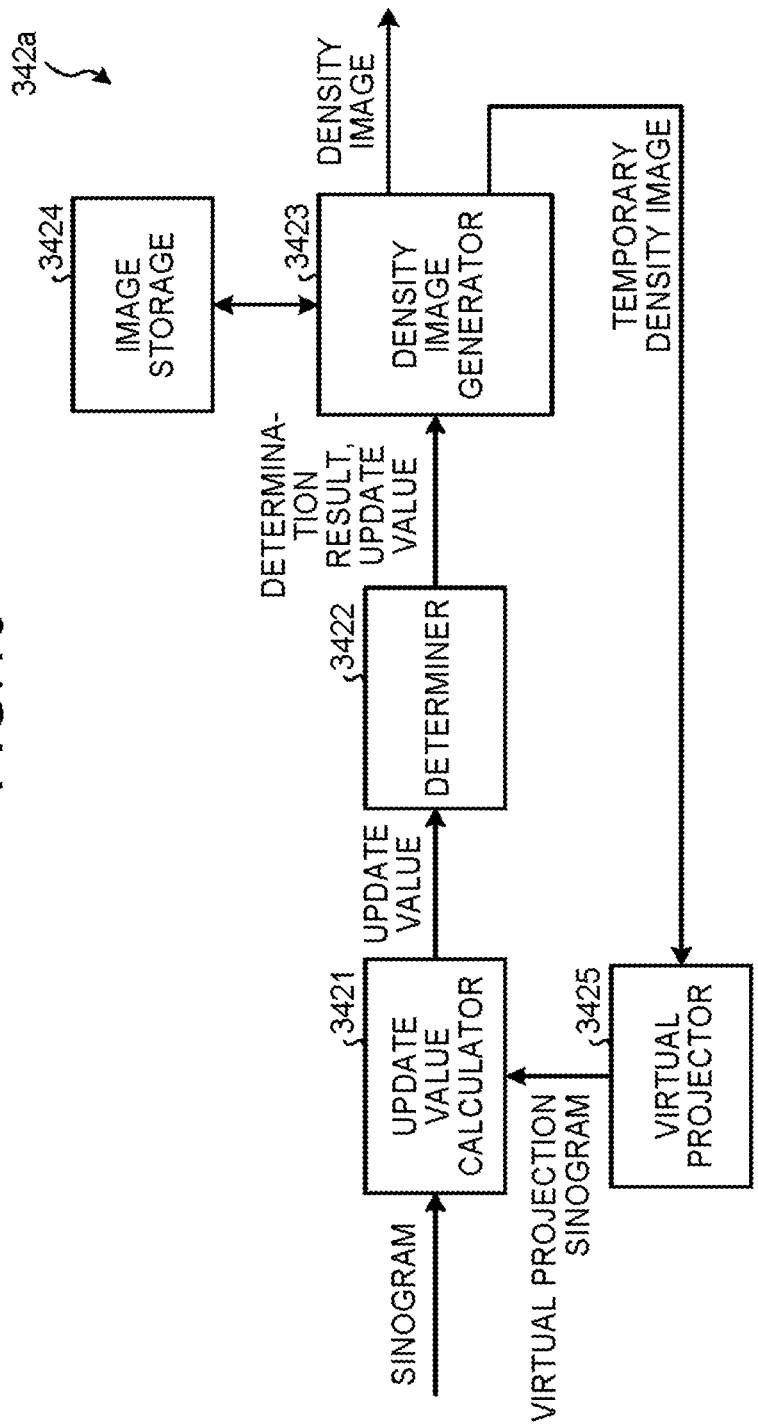
FIG. 10 is a diagram illustrating an example of a block configuration of a first generator of an image processor according to a second embodiment.
Figure 11:
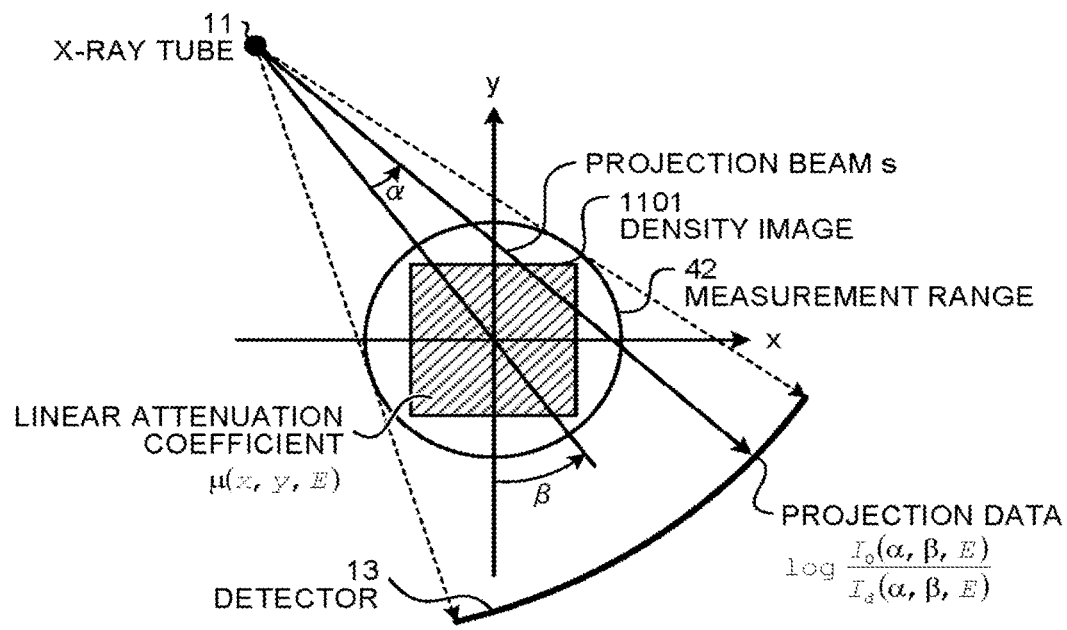
FIG. 11 is a diagram for explaining a relation between projection data and the linear attenuation coefficient.
Figure 12:
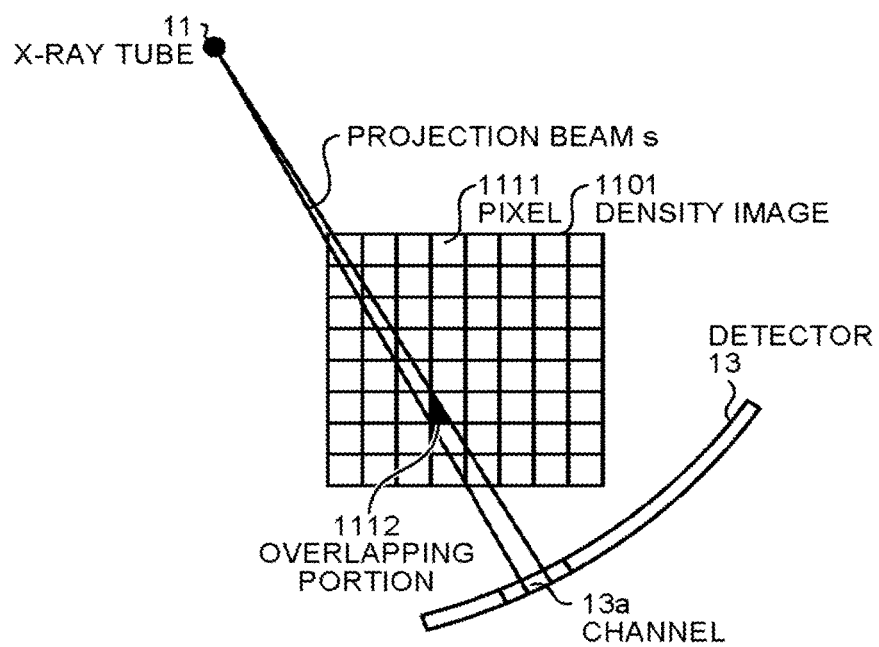
FIG. 12 is a diagram for explaining a contribution degree of pixels.

FIG. 10 is a diagram illustrating an example of a block configuration of a first generator of the image processor according to the second embodiment. FIG. 11 is a diagram for explaining a relation between the projection data and the linear attenuation coefficient. FIG. 12 is a diagram for explaining a contribution degree of pixels. With reference to FIGS. 10 to 12, the following describes the block configuration of a first generator 342a of the image processor according to the second embodiment and the operation of each block.

In the configuration of the image processor according to the second embodiment, the first generator 342 of the image processor 34 according to the first embodiment illustrated in FIG. 5 is replaced with the first generator 342a illustrated in FIG. 10. In other words, similarly to the first generator 342, the first generator 342a is a functional unit that receives a subject sinogram input from the projection data acquirer 341, and generates a density image to be output to the second generator 343. As illustrated in FIG. 10, the first generator 342a includes an update value calculator 3421 (calculator, second comparator), a determiner 3422 (second determiner), a density image generator 3423 (updater, fourth generator), an image storage 3424, and a virtual projector 3425 (third generator, fifth generator).

The update value calculator 3421 is a functional unit that calculates a difference (second difference) that is a result of comparison between an attenuation factor sinogram generated from the subject sinogram received from the projection data acquirer 341 and a virtual projection sinogram (temporary projection data) generated by the virtual projector 3425, and generates an update value for each pixel so that the difference is reduced.

Specifically, the update value calculator 3421 first sets a specific energy band, receives a subject sinogram of the set energy band from the projection data acquirer 341, and generates an attenuation factor sinogram from the received subject sinogram. A method of calculating the attenuation factor as the pixel value of the attenuation factor sinogram is the same as the method described in the first embodiment. When the number of photons in a case in which the subject 40 is placed is assumed to be A, and the number of photons in a case in which the subject 40 is not placed is assumed to be B, for example, log(B/A) can be calculated to be the pixel value (attenuation factor) of the attenuation factor sinogram.

Next, the update value calculator 3421 receives the virtual projection sinogram from the virtual projector 3425, and calculates a difference D between the virtual projection sinogram and the attenuation factor sinogram for each channel, each view, and each energy (energy band) through the following Equation (2). In other words, the update value calculator 3421 calculates the difference D between the attenuation factor sinogram of each of the set energy bands and the virtual projection sinogram for each pixel.

$$D = \text{(the pixel value of the virtual projection sinogram)} - \text{(the pixel value of the attenuation factor sinogram)} \quad (2)$$

If the difference D calculated by the update value calculator 3421 is represented as D>0, the density, the mass, and the linear attenuation coefficient of the material set by the density image generator 3423 described later are all positive values, so that the difference D is reduced as the pixel value of a temporary density image generated by the density image generator 3423 described later is reduced. For example, the update value calculator 3421 calculates, as the update value (>0) for each material, a value by multiplying the difference D by the contribution degree of each pixel of the temporary density image for the channel and the view, $(\mu)(E)/(\rho)_M$ (refer to Equation (1) described above) at the energy for each material, and an adjustment parameter that is separately specified. As described later, the density image generator 3423 subtracts the update value calculated by the update value calculator 3421 from the pixel value of the temporary density image for each material.

On the other hand, if the difference D calculated by the update value calculator 3421 is represented as D<0, the difference D is reduced as the pixel value of the temporary density image generated by the density image generator 3423 described later is increased. Similarly to the above process, the update value calculator 3421 calculates the update value (<0) for each material. As described later, the density image generator 3423 subtracts the update value calculated by the update value calculator 3421 from the pixel value of the temporary density image for each material. In this case, the update value is a negative value, so that the pixel value of the temporary density image is increased.

If the difference D calculated by the update value calculator 3421 is represented as D=0, (the pixel value of) the virtual projection sinogram is identical to (the pixel value of) the attenuation factor sinogram, so that the update value calculator 3421 does not calculate the update value. Alternatively, in this case, the update value calculator 3421 causes the update value to be 0.

The update value calculator 3421 transmits the calculated update value to the determiner 3422. Upon receiving the change information from the changer 346 (refer to FIG. 5), the update value calculator 3421 changes, for example, the set energy band according to the change information, receives a subject sinogram of the energy band the setting of which is changed from the projection data acquirer 341 again, and calculates the update value described above.

The determiner 3422 is a functional unit that determines whether the update value calculated by the update value calculator 3421 is equal to or smaller than a predetermined value. If the update value is equal to or smaller than the predetermined value (third predetermined value), it can be determined that the pixel value of the temporary density image generated by the density image generator 3423 described later comes close to correct density. The determiner 3422 transmits a determination result of the update value and the update value received from the update value calculator 3421 to the density image generator 3423. Actually, the update value may take a positive/negative value as described above, so that determination may be made on the absolute value of the update value. The determiner 3422 is assumed to determine whether the update value is equal to or smaller than the predetermined value. However, embodiments are not limited to this. The determiner 3422 may determine whether the number of times of determination (that is, the number of times of update processing performed by the density image generator 3423 described later) reaches a predetermined number of times.

The density image generator 3423 is a functional unit that reads out and acquires a provisional density image (hereinafter, referred to as "temporary density image") stored in the image storage 3424, and successively updates the temporary density image with the update value received from the determiner 3422. Specifically, the density image generator 3423 first sets the materials that are possibly present in the subject 40, and reads out and acquires an initial temporary density image from the image storage 3424 for each of the set materials. The initial temporary density image is, for example, an image in which all pixel values are constant values. Next, the density image generator 3423 subtracts the update value received from the determiner 3422 from the pixel value of the temporary density image to update the temporary density image. The density image generator 3423 causes the image storage 3424 to store therein the updated temporary density image, and transmits the temporary density image to the virtual projector 3425. If the determination result received from the determiner 3422 indicates that the update value is equal to or smaller than the predetermined value, the density image generator 3423 transmits the updated temporary density image to the second generator 343 (refer to FIG. 5) as a proper density image. Upon receiving the change information from the changer 346 (refer to FIG. 5), the density image generator 3423 changes, for example, the setting of the materials that are possibly present in the subject 40 according to the change information, and performs update processing again on the initial temporary density image.

As described above, the image storage 3424 is a functional unit that stores therein the initial temporary density image and the updated temporary density image. The image storage 3424 is, for example, implemented with a storage device that is not illustrated. The image storage 3424 may be implemented with the image storage 35 illustrated in FIG. 1.

The virtual projector 3425 is a functional unit that generates a virtual projection sinogram for each channel, each view, and each energy (energy band) that are the same as those of the attenuation factor sinogram from the temporary density image for each material received from the density image generator 3423.

In this case, the linear attenuation coefficient $\mu(x, y, E)$ of the reconstructed image reconstructed from the attenuation factor sinogram of each energy (energy band) is calculated through Equation (1) described above using the density $\rho(x, y, M)$.

Assuming that the channel is $\alpha$, the view is $\beta$, the number of photons of the energy E of X-rays in a case in which the subject 40 is placed is $I_d(\alpha, \beta, E)$, and the number of photons of the energy E of X-rays in a case in which the subject 40 is not placed is $I_0(\alpha, \beta, E)$, the pixel value $\log(I_0(\alpha, \beta, E)/I_d(\alpha, \beta, E))$ of the virtual projection sinogram is an integral along a path (in this case, referred to as s) of a projection beam s illustrated in FIG. 11, and is represented by the following Equation (3).

$$\log \frac{I_0(\alpha, \beta, E)}{I_d(\alpha, \beta, E)} = \int \mu(x, y, E) ds \quad (3)$$

When the linear attenuation coefficient $\mu(x, y, E)$ represented by Equation (1) is substituted in Equation (3), the following Equation (4) can be obtained.

$$\log \frac{I_0(\alpha, \beta, E)}{I_d(\alpha, \beta, E)} = \sum_M \left[ \frac{(\mu)_M(E)}{(\rho)_M} \int \rho(x, y, M) ds \right] \quad (4)$$

The virtual projector 3425 calculates the pixel value $\log(I_0(\alpha, \beta, E)/I_d(\alpha, \beta, E))$ of the virtual projection sinogram from the density $\rho(x, y, M)$ as the pixel value of the temporary density image for each of set materials M through Equation (4), and generates a virtual projection sinogram for each channel, each view, and each energy (energy band) that are the same as those of the attenuation factor sinogram. In other words, the virtual projector 3425 first integrates the density of each of the materials M along the path of the projection beam s determined corresponding to the channel and the view for each channel, each view, and each energy E, and adds the values obtained by multiplying $(\mu)_M(E)/(\rho)_M$ in a case in which the concentration of the material M is 100 [%] for all of the materials M.

Actually, the temporary density image is discrete data, so that the integral along the path of the projection beam s is, as illustrated in FIG. 12 for example, such that a black-filled area of an overlapping portion 1112 of the projection beam s leading to each channel 13a and a pixel 1111 among pixels 1111 included in a density image 1101 is caused to be the contribution degree of the pixel (normalized with the projection beam s as needed). The virtual projector 3425 then causes a value obtained by adding a product of the pixel value and the contribution degree to be an integral value of the density $\rho$ for the pixel overlapping with the projection beam s in the density image 1101.

The virtual projector 3425 transmits the generated virtual projection sinogram to the update value calculator 3421.

The pixel value is not necessarily updated for each group of the channel, the view, and the energy. For example, when the pixel value is updated with each of update values organized for all channels for each group of a certain view and certain energy, the channels can be processed in parallel, which can reduce a processing time. Similarly, the same effect can be obtained when the update values are organized for each view or each energy.

The result of comparison (for example, information on the difference) between the attenuation factor sinogram and the virtual projection sinogram obtained by the update value calculator 3421 may be displayed, for example, on the display device 32 (an example of a second notifier). In this case, a method for sending a notification indicating the result of comparison is not limited to the display on the display device 32. For example, the result of comparison may be provided with audio output by an audio output device (an example of the second notifier) not illustrated, or provided with lighting or flashing of a lamp by a lamp display device (an example of the second notifier). For example, a result of comparison may be obtained by the update value calculator 3421 after the following operations are repeated until a predetermined number of times is reached: the update value calculator 3421 receives a sonogram of specific energy and calculates an update value, the determiner 3422 makes a determination, the density image generator 3423 updates a temporary density image with the update value, and the virtual projector 3425 generates a virtual projection sonogram. The result of comparison may then be displayed on the display device 32. In this case, for example, the above-described repeat of operations may be continued after an operator who has checked the result of comparison displayed on the display device 32 changes the setting of a material the density of which is calculated or the energy band of the sonogram through the input device 31.

The update value calculator 3421, the determiner 3422, the density image generator 3423, the image storage 3424, and the virtual projector 3425 illustrated in FIG. 10 are merely conceptual functions, and the configuration is not limited to this. For example, a plurality of functional units illustrated as independent functional units in FIG. 10 may be configured as one functional unit. On the other hand, a function of one functional unit in FIG. 10 may be divided into a plurality of functions to be configured as a plurality of functional units.

Figure 13:
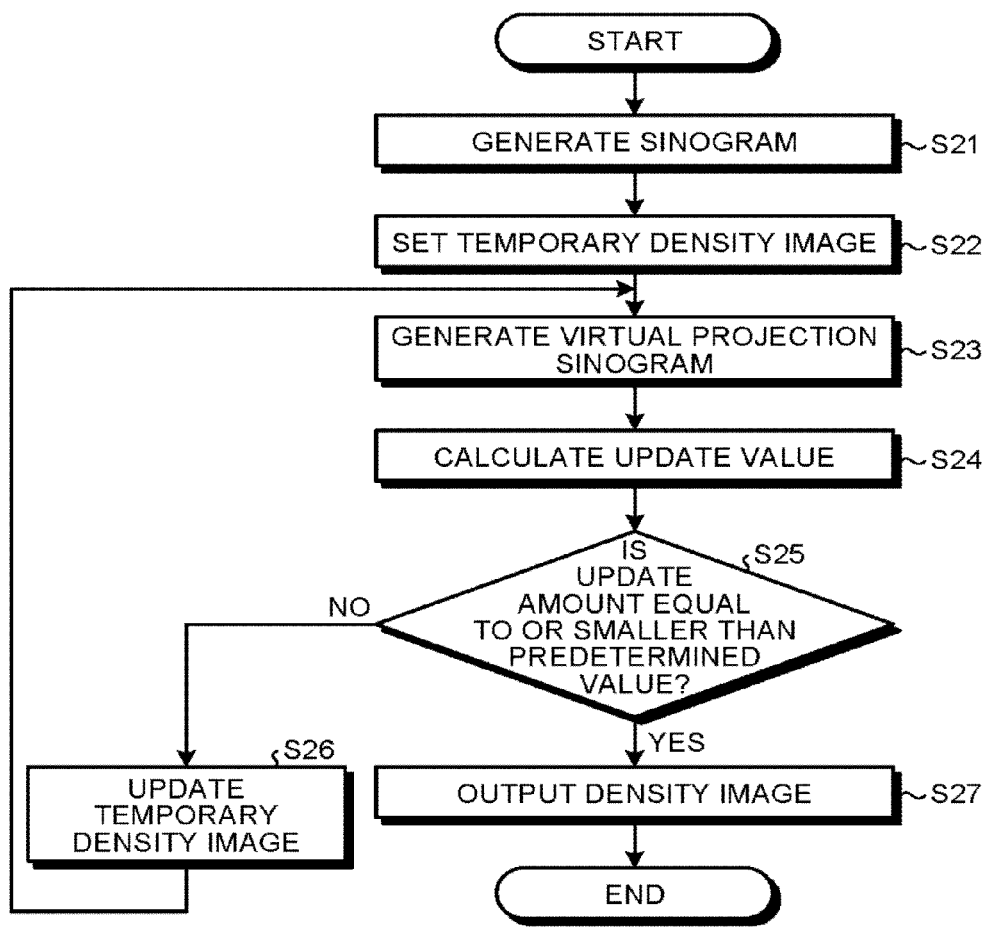
FIG. 13 is a flowchart illustrating an example of an operation of the image processor according to the second embodiment.

FIG. 13 is a flowchart illustrating an example of an operation of the image processor according to the second embodiment. With reference to FIG. 13, the following mainly describes an operation of generating a density image performed by the first generator 342a of the image processor according to the second embodiment. The image processing performed by the image processor is the same as the image processing performed by the image processor 34 according to the first embodiment except density image processing performed by the first generator 342a.

Step S21

The projection data acquirer 341 (refer to FIG. 5) receives and acquires, as the projection data, the subject sinogram as a sinogram of the subject 40 generated by the data collector 16 (refer to FIG. 1). The update value calculator 3421 sets a specific energy band, receives a subject sinogram of the set energy band from the projection data acquirer 341, and generates an attenuation factor sinogram from the received subject sinogram. Then the process proceeds to Step S22.

Step S22

The density image generator 3423 sets the materials that are possibly present in the subject 40, and reads out and acquires (sets) an initial temporary density image from the image storage 3424 for each of the set materials. The density image generator 3423 transmits the acquired temporary density image to the virtual projector 3425. Then the process proceeds to Step S23.

Step S23

The virtual projector 3425 calculates the pixel value $\log(I_0(\alpha, \beta, E)/I_d(\alpha, \beta, E))$ of the virtual projection sinogram from the density $\rho(x, y, M)$ as the pixel value of the temporary density image for each of the set materials through Equation (4), and generates a virtual projection sinogram for each channel, each view, and each energy (energy band) that are the same as those of the attenuation factor sinogram. The virtual projector 3425 transmits the generated virtual projection sinogram to the update value calculator 3421. Then the process proceeds to Step S24.

Step S24

The update value calculator 3421 receives the virtual projection sinogram from the virtual projector 3425, and calculates the difference D between the virtual projection sinogram and the attenuation factor sinogram for each channel, each view, and each energy (energy band) through the above Equation (2). In other words, the update value calculator 3421 calculates the difference D between the attenuation factor sinogram of each of the set energy bands and the virtual projection sinogram for each pixel. Next, the update value calculator 3421 calculates, as the update value for each material, a value by multiplying the difference D by the contribution degree of each pixel of the temporary density image for the channel and the view, $(\mu)_M(E)/(\rho)_M$ (refer to Equation (1)) at the energy for each material, and the adjustment parameter that is separately specified. The update value calculator 3421 transmits the calculated update value to the determiner 3422. Then the process proceeds to Step S25.

Step S25

The determiner 3422 determines whether the update value calculated by the update value calculator 3421 is equal to or smaller than a predetermined value. If the update value is equal to or smaller than the predetermined value, it can be determined that the pixel value of the temporary density image generated by the density image generator 3423 comes close to correct density. The determiner 3422 transmits a determination result of the update value and the update value received from the update value calculator 3421 to the density image generator 3423. If the update value is equal to or smaller than the predetermined value (Yes at Step S25), the process proceeds to Step S27. If the update value is larger than the predetermined value (No at Step S25), the process proceeds to Step S26.

Step S26

The density image generator 3423 reads out and acquires the temporary density image stored in the image storage 3424, and successively updates the temporary density image with the update value received from the determiner 3422. Specifically, the density image generator 3423 subtracts the update value received from the determiner 3422 from the pixel value of the temporary density image to update the temporary density image. The density image generator 3423 then causes the image storage 3424 to store therein the updated temporary density image, and transmits the temporary density image to the virtual projector 3425. Then the process returns to Step S23.

Step S27

If the determination result received from the determiner 3422 indicates that the update value is equal to or smaller than the predetermined value, the density image generator 3423 outputs the updated temporary density image (the temporary density image read out from the image storage 3424) to the second generator 343 (refer to FIG. 5) as a proper density image.

The series of operations at Steps S23 to S26 are repeated until the density of the updated temporary density image is a correct value (Step S25), that is, the update value is repeatedly calculated by the update value calculator 3421 and the temporary density image is repeatedly updated by the density image generator 3423. The operations may be repeated until the predetermined number of times is reached as described above.

As described above, the processing based on successive approximation is performed such that the virtual projector 3425 generates a virtual projection sinogram from the temporary density image received from the density image generator 3423 using Equation (4), the update value calculator 3421 calculates the update value based on the difference between the virtual projection sinogram and the attenuation factor sinogram, and the density image generator 3423 updates the temporary density image with the update value calculated by the update value calculator 3421. If the determiner 3422 determines that the update value (absolute value) calculated by the update value calculator 3421 is equal to or smaller than the predetermined value, the density image generator 3423 determines that the pixel value of the updated temporary density image to be correct density, and outputs the updated temporary density image as a proper density image. In this process, the density image can be directly obtained without obtaining the linear attenuation coefficient from the attenuation factor sinogram, so that error occurrence can be suppressed as compared with a case of obtaining the linear attenuation coefficient in midstream.

In a case of generating the reconstructed image constructed with the linear attenuation coefficient from the sinogram, and further generating a density image from the reconstructed image, both of the reconstructed image and the density image need to be stored in a storage. However, in the present embodiment, the density image is directly obtained from the sinogram, so that only the density image needs to be stored. Accordingly, the capacity of the storage required can be reduced.

In the embodiments described above, the X-ray inspecting device 1 is assumed to be the spectral CT device or the photon counting CT device. However, the embodiments are not limited to these. For example, a dual energy CT device may be used as the X-ray inspecting device 1. In a case of the dual energy CT device, the accuracy of the density image can be determined by generating the subject sinogram and the attenuation factor sinogram in two types of energy bands of the X-rays emitted with high and low tube voltages, causing two energy bands in calculating the density of two materials to be energy bands determined depending on the tube voltages, and causing the difference comparison energy to be any one or both of the energy bands determined depending on the tube voltages. If the difference is large, the accuracy of the density image may be improved by changing the type of the material. A multi-energy CT device can also be used as the X-ray inspecting device 1.

The image processing device (console device 30) according to the embodiments and the modification described above has a configuration utilizing a computer. In other words, the console device 30 includes a control device (for example, the scan controller 33 and the system controller 36 in FIG. 1) such as a central processing unit (CPU), a storage device such as a read only memory (ROM) or a random access memory (RAM), an external storage device (for example, the image storage 35 in FIG. 1) such as a hard disk drive (HDD) or a CD drive, an input device (the input device 31 in FIG. 1) such as a keyboard or a mouse, and a display device (the display device 32 in FIG. 1) such as a display.

As described above, when at least one of the group of the projection data acquirer 341, the first generator 342, the second generator 343, the reconstructor 344, the difference determiner 345, and the changer 346, and the group of the update value calculator 3421, the determiner 3422, the density image generator 3423, and the virtual projector 3425 is implemented as a computer program, the computer program to be executed by the console device 30 is recorded in a computer-readable recording medium such as a CD-ROM, a flexible disk (FD), a CD-R, or a digital versatile disc (DVD) as an installable or executable file to be provided as a computer program product.

The computer program to be executed by the image processing device (console device 30) according to the embodiments and the modification described above may be stored in a computer connected to a network such as the Internet and provided by being downloaded via the network. Furthermore, the computer program to be executed by the image processing device (console device 30) according to the embodiments and the modification described above may be provided or distributed via a network such as the Internet. The computer program may be embedded and provided in a ROM, for example.

The computer program to be executed by the image processing device (console device 30) according to the embodiments and the modification described above has a module configuration including at least one of the group of the projection data acquirer 341, the first generator 342, the second generator 343, the reconstructor 344, the difference determiner 345, and the changer 346, and the group of the update value calculator 3421, the determiner 3422, the density image generator 3423, and the virtual projector 3425. As actual hardware, the CPU reads out and executes the computer program from the storage medium described above, and each of the functional units is loaded and generated on the main storage device. Part or all of the functional units of the image processing device described above may be implemented as a hardware circuit instead of the computer program as software.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:
    processing circuitry configured to:
        acquire projection data that is based on a spectrum representing an amount of X-rays with respect to energy of a radiation having passed through a subject;
        select a plurality of materials;
        generate, from the projection data, first density images for each of the selected materials;
        generate a monochromatic image of specific energy from the first density images;

reconstruct the projection data corresponding to the specific energy to generate a reconstructed image;
compare the monochromatic image and the reconstructed image; and
provide a notification indicating a result of the comparison.

2. The X-ray computed tomography (CT) apparatus according to claim 1, wherein the processing circuitry further re-selects materials based on the result of the comparison, and further generates, from the projection data, a second density image for each of the re-selected materials.

3. The X-ray computed tomography (CT) apparatus according to claim 2, wherein the processing circuitry
calculates a first difference between pixel values of the monochromatic image and the reconstructed image as the result of the comparison; and
makes a determination based on the first difference whether to generate the second density image.

4. The X-ray computed tomography (CT) apparatus according to claim 3, wherein the processing circuitry
determines whether a value obtained based on the first difference is larger than a first predetermined value; and
generates the second density image when the value obtained based on the first difference is larger than the first predetermined value.

5. The X-ray computed tomography (CT) apparatus according to claim 3, wherein the processing circuitry changes the selected materials or changes energy corresponding to the projection data for generating the second density image, based on the determination.

6. The X-ray computed tomography (CT) apparatus according to claim 5, wherein the processing circuitry
refers to priority information in which materials assumed to be present in the subject are associated with priorities; and
adds and changes a material as one of the materials to be selected in order from a material having higher priority in the priority information.

7. The X-ray computed tomography (CT) apparatus according to claim 5, wherein the processing circuitry
generates the monochromatic image while continuously switching magnitude of the specific energy; and
selects a material having a K-absorption edge at the specific energy at which a change amount of the first difference exceeds the second predetermined value in accordance with the continuous switching of the magnitude of the specific energy.

8. The X-ray computed tomography (CT) apparatus according to claim 3, wherein the processing circuitry calculates the first difference between the entire monochromatic image and the entire reconstructed image.

9. The X-ray computed tomography (CT) apparatus according to claim 3, wherein the processing circuitry calculates the first difference between the monochromatic image and the reconstructed image for each pixel or each region.

10. The X-ray computed tomography (CT) apparatus according to claim 3, wherein the processing circuitry
generates a plurality of the monochromatic images for each of pieces of the specific energy from the first density images;
reconstructs the projection data corresponding to each of the pieces of the specific energy to generate the reconstructed image; and
calculates the first difference between each of the monochromatic images and the reconstructed images corresponding to each of the monochromatic images.

11. The X-ray computed tomography (CT) apparatus according to claim 2, wherein the processing circuitry
receives an instruction; and
generates the second density image according to the instruction based on the result of the comparison.

12. The X-ray computed tomography (CT) apparatus according to claim 11, wherein the processing circuitry changes the materials to be selected or changes the energy corresponding to the projection data for generating the second density image to generate the second density image, based on the instruction.

13. The X-ray computed tomography (CT) apparatus according to claim 1, wherein the processing circuitry
generates temporary density images that are provisional density images of each of the materials;
generates temporary projection data that is provisional projection data for each of a plurality of pieces of energy from the temporary density images;
calculates a second difference between pixel values of the projection data and the temporary projection data, and calculate an update value based on the second difference;
makes a determination on the update value; and
updates the temporary density image with the update value, and outputs, as the first density image, the temporary density image when an absolute value of the update value is equal to or smaller than a third predetermined value.

14. The X-ray computed tomography (CT) apparatus according to claim 1, further comprising:
an X-ray tube configured to emit the radiation around the subject; and
a detector configured to detect energy of the radiation emitted from the X-ray tube.

15. An X-ray computed tomography (CT) apparatus comprising:
processing circuitry configured to:
acquire projection data that is based on a spectrum representing an amount of X-rays with respect to energy of a radiation having passed through a subject;
select a plurality of materials;
generate density images for each the selected materials based on the projection data;
generate temporary projection data that is provisional projection data for each of a plurality of pieces of energy from the density image; and
compare the projection data corresponding to each of the pieces of the energy and the temporary projection data.

16. The X-ray computed tomography (CT) apparatus according to claim 15, wherein the processing circuitry
provides a notification indicating a result of the comparison.

17. The X-ray computed tomography (CT) apparatus according to claim 15, further comprising:
an X-ray tube configured to emit the radiation around the subject; and
a detector configured to detect energy of the radiation emitted from the X-ray tube.

18. An image processing device comprising:
processing circuitry configured to:
acquire projection data based on a spectrum representing an amount of X-rays with respect to energy of a radiation that has passed through a subject;
select a plurality of materials;

generate, from the projection data, first density images for each of the selected materials;
generate a monochromatic image of specific energy from the first density images;
reconstruct the projection data corresponding to the specific energy to generate a reconstructed image;
compare the monochromatic image and the reconstructed image; and
provide a notification indicating a result of the comparison.

* * * * *